US006322251B1

(12) United States Patent
Ballhaus et al.

(10) Patent No.: US 6,322,251 B1
(45) Date of Patent: Nov. 27, 2001

(54) OPERATING TABLE SYSTEM

(75) Inventors: Heribert Ballhaus, Heroldsberg; Jan Donat Olszewski, Karlsruhe; Klaus Sutter, Rastatt, all of (DE)

(73) Assignee: Maquet AG, Rastatt (DE)

( * ) Notice: Subject to any disclaimer, the term of this patent is extended or adjusted under 35 U.S.C. 154(b) by 0 days.

(21) Appl. No.: 09/414,285

(22) Filed: Oct. 7, 1999

(30) Foreign Application Priority Data

Oct. 9, 1998 (DE) .......................................... 298 18 100 U

(51) Int. Cl.[7] ............................... A61B 6/04; A61G 13/00
(52) U.S. Cl. .......................... 378/209; 378/195; 378/208
(58) Field of Search .................................... 378/209, 208, 378/195, 4; 5/601, 510, 511

(56) References Cited

U.S. PATENT DOCUMENTS

| 4,576,368 | 3/1986 | Ogawa et al. . | |
| 4,727,328 | * 2/1988 | Carper et al. | 378/209 |
| 4,914,682 | * 4/1990 | Blumenthal | 378/209 |
| 5,475,884 | 12/1995 | Kirmse et al. | 378/209 |
| 5,499,415 | * 3/1996 | McKenna | 378/209 |
| 5,619,763 | * 4/1997 | Randolph et al. | 378/209 |
| 5,638,419 | 6/1997 | Ingweren | 378/208 |

FOREIGN PATENT DOCUMENTS

| 92 18 321 | 1/1994 | (DE) . |
| 92 18 322 | 1/1994 | (DE) . |
| 195 33 098 A1 | 11/1996 | (DE) . |
| 1014630 | 12/1965 | (GB) . |
| 2 057 830 A | 4/1981 | (GB) . |

* cited by examiner

Primary Examiner—Drew Dunn
(74) Attorney, Agent, or Firm—McCormick, Paulding & Huber LLP

(57) ABSTRACT

In an operating table system for the computer tomography assisted performance of operations on patients, including an operating table 10 with a subframe 14 and a patient support surface 12 releasably connected with the subframe, the patient support surface means 12 has a frame 16 connected with the subframe 14 and an x-ray permeable patient support plate 20 longitudinally slidably carried in the frame 16, with a support frame 44 intended for the reception of the support plate in a computer tomography system 40 having coupled with it a coupling station 46 for the transfer of the support plate from the operating table 10 to the support frame 44 and vice versa.

8 Claims, 2 Drawing Sheets

OPERATING TABLE SYSTEM

FIELD OF THE INVENTION

The invention concerns an operating table system for computer tomography supported operations on patients, including an operating table with a subframe and a patient support means releasably connected with the subframe.

BACKGROUND OF THE INVENTION

The creation of computer tomography (CT) pictures for diagnostic purposes and for preparing for operations is known. In this case the patient is customarily laid on a table unit arranged in front of the computer tomography system and its table plate is one which can be moved into the computer tomography system. If the patient is to be operated on immediately following this, he must be rebedded from this table onto the support surface of the operating table. With such a previously described process it is not possible during an operation to create a supplemental computer tomography picture since the patient during the operation cannot be moved, and in any event cannot have his support changed from the support surface of the operating table to another support.

The invention has as its object the provision of an operating table system of the above-mentioned kind which makes it possible to analyse the patient during an operation in a computer tomography system, which computer tomography system can be arranged directly in the vicinity of the operating room.

SUMMARY OF THE INVENTION

This object is solved in accordance with the invention in that the patient support surface means has a frame connected with the subframe and an x-ray permeable patient support plate longitudinally slidably guided in the frame and in that a support frame for receiving the support plate in a computer tomography device has a coupling station for transfer of the support plate from the operating table to the support frame and vice versa is connected.

By way of the solution of the invention, a patient can be moved from the operating table into the computer tomography system without him having to be moved on the support plate. Therefore, it is possible for example, to make a control picture by the computer tomography system during an operation and at the end of the operation without the patient having to be rebedded from the operating table support surface onto another under support.

Preferably, the coupling station has a drive for shifting the support plate from the subframe onto the support frame and vice versa, with this drive also being usable for moving the patient into the computer tomography system.

The drive can, for example, have drive rollers or gears, which shape-wise or force-wise grip the support plate. In keeping with this, the drive can at least include a motor driven or a toothed belt, which is designed to come into mesh with a rack provided on the patient support plate.

The patient support surface means can in a usual way be divided into several sections which are connected with one another so as to be pivotal about horizontal axes. In this case, the sections of the support plate which are pivotally movable relative to one another are preferably connected with one another by sheet hinges, so that no x-ray efficiency influencing metal hinges are necessary. In order that the patient can be moved as quickly, vibration-free and precisely as possible to the coupling station, it is practical if the subframe is shiftable on a guide track extending to the coupling station.

In order to have the possibility of having the x-rays pass through the person lying on the operating table, it is practical if the subframe has at least two support columns carrying the frame, which support columns are movable relative to one another or in common manually or by motor shifting on the guide tracks. In this way the space below the patient support surface means can sectionally be made entirely free in order to be able to push an x-ray device under the involved section of the patient support surface means. There also thereby exists the possibility to support different sections of the patient support surface if the other sections are to be moved to achieve specific body positions of the patient.

In a preferred embodiment of the invention the frame of the operating table has two longitudinal beams on which first guide tracks for the patient support plate and second guide tracks for cross beams connected with the support columns are formed. The sub-frame and the individual support columns can be adjustable in height.

Further features and advantages of the invention will be apparent from the following description which explains the invention by way of an exemplary embodiment in connection with the accompanying drawings.

DETAILED DESCRIPTION OF THE PREFERRED EMBODIMENT

Figure 1:
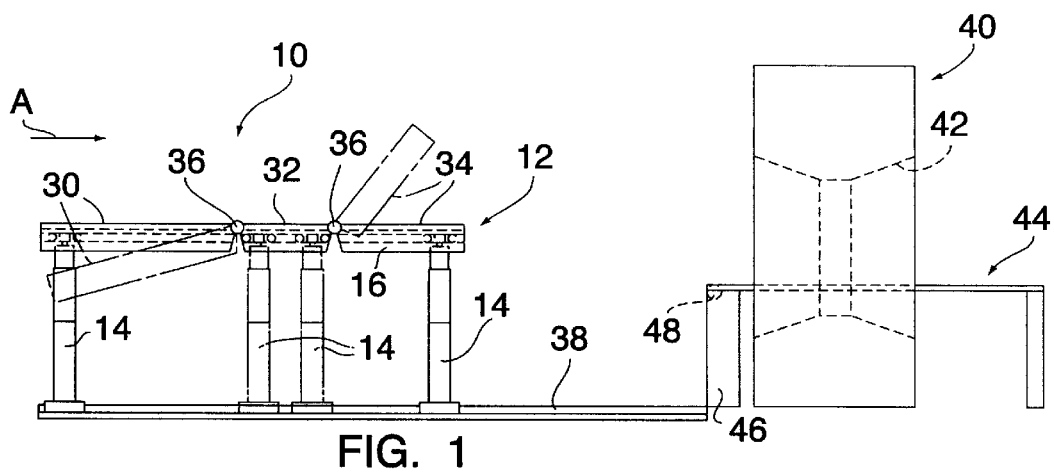
FIG. 1—a schematic side view of an operating table system embodying the invention with a computer tomography apparatus.
Figure 2:
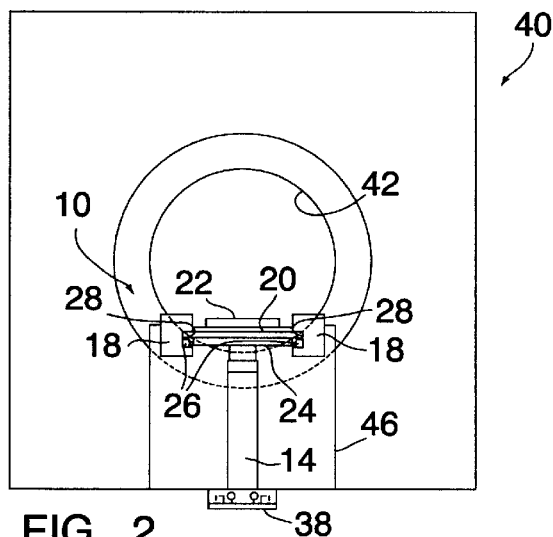
FIG. 2—an end view of the table system of FIG. 1 taken in the the direction of the arrow A of FIG. 1.

In FIG. 1 is seen an operating table, indicated generally at 10, with a patient support surface means 12, which rests on two support columns 14 which form the subframe.

The patient support surface means 12 includes a frame 16 with two longitudinal beams 18 which are connected to one another by a frame plate 22 made of an x-ray permeable material, for example hard paper. A patient support plate 20 lies on the frame plate 22, with the patient support plate 20 being slidable on sliding guides with respect to the frame plate in the longitudinal direction. The upper end of each support column 14 has fastened to it a cross beam 24 which carries rollers 26 at its free end by means of which rollers the cross beam 24 is shiftably guided in the grooves 28 of the longitudinal beams 18. The rollers 26 can be locked in the grooves 28 so that the beam 24 can selectively and individually be connected with the patient support means 12 or can be made shiftable relative to the patient support means.

The longitudinal beams 18 and the frame plate 22 in the illustrated embodiment are divided into three sections 30, 32 and 34 which are connected with one another by joints 36 so that they can be pivoted relative to one another about horizontal pivot axis, as is indicated in FIG. 1 by the broken line illustrated positions of the sections 30 and 34. The support plate 20 has at the positions corresponding to the joints 36 also joints so that the support plate can follow the pivotal moment of the section 30 and 34. Since the support plate 20 should be permeable to x-rays, it consists preferably of plastic. To not influence the effectiveness of the x-rays the corresponding hinges between the sections of the support plate 20 are formed from sheet-type hinges or as some other type of x-ray permeable hinges.

The columns 14 are shiftable on a guide track 38 fastened to or inset into the floor, so that they can be adjusted relative to one another, as illustrated by the broken line columns shown in FIG. 1 which support the middle section 32 of the patient support means 12. Further, the operating table 10 in its entirety can be adjusted on the guide tracks 38 in the direction toward the computer tomography apparatus 40. The computer tomography apparatus 40 is of a customary type and need not be explained in more detail. It has a central opening 42 through which extends a table shaped supporting frame 44, which on its side facing the operating table 10 is connected with a coupling station 46. The support frame 44 serves to receive the support plate 20, the coupling station 46 having a drive indicated by a roll 48, for the purpose of pulling the support plate 20 from the operating table 10 and onto the support frame 44. This can, for example, be so accomplished in that the roll 48 is gear driven by a non-illustrated motor and in that the gear meshes with a non-illustrated rack provided on the support plate 20. It is also possible that the drive could include friction rollers which transport the support plate 20.

Figure 3:
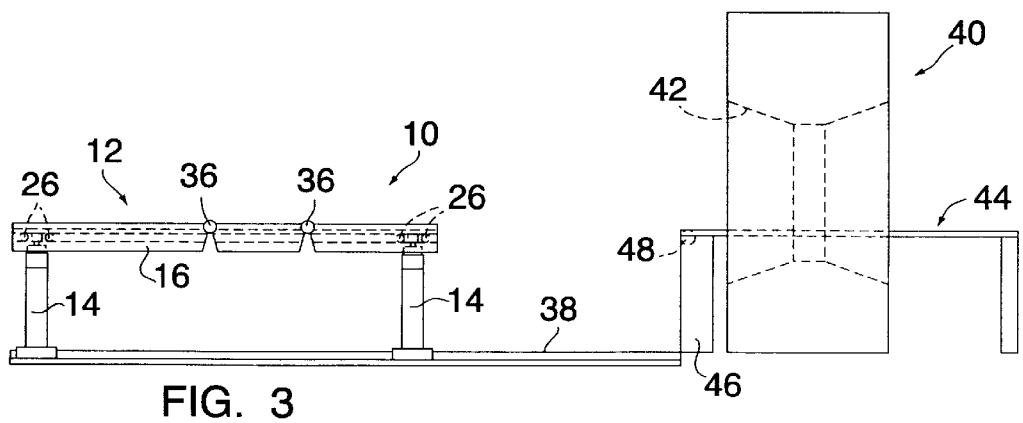
FIGS. 3–6—side views corresponding to FIG. 1 of the inventive operating table system in different phases in the transfer of the patient supporting plate from the operating table to the supporting frame inside of the computer tomography apparatus.
Figure 4:
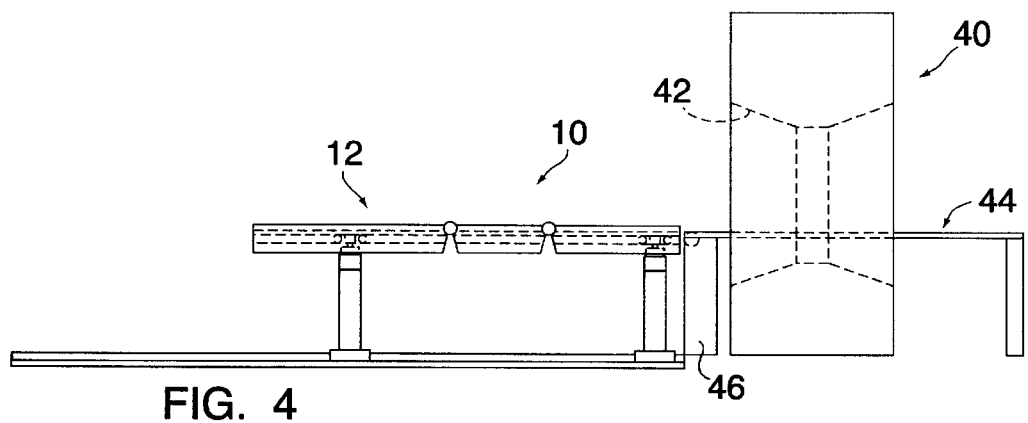
Figure 5:
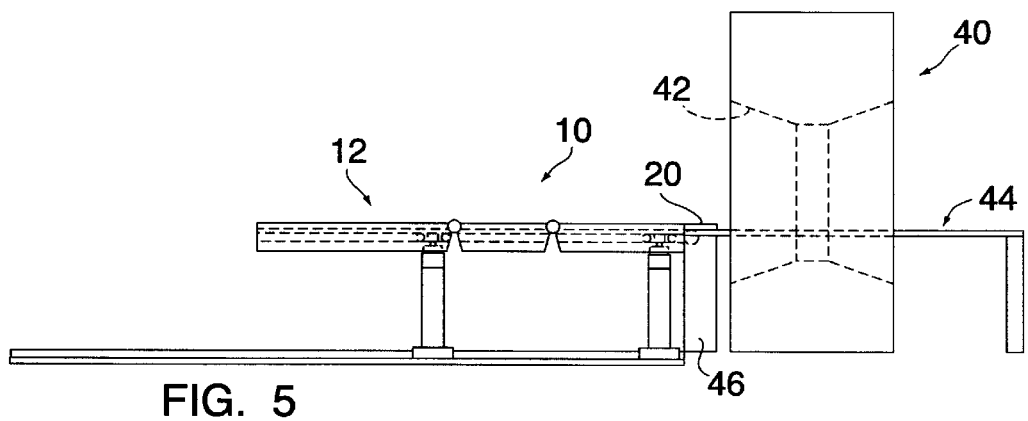
Figure 6:
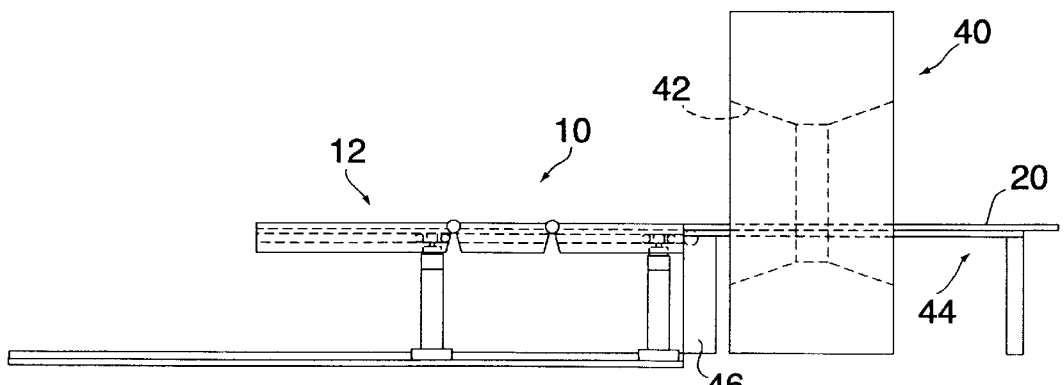

The transfer occurs in such way that the patient support means 12 is first lowered (or if required lifted) from the operation position illustrated in FIGS. 1 to the level illustrated in FIG. 3, at which the support plate 20 is at a height (FIG. 3) corresponding to that of the support frame 44. Then the operating table, according to FIG. 4, is moved forward to the coupling station 46 and the support plate 20, according to FIG. 5, is brought into grip with the drive element 48 of the coupling station 46. Then the support plate together with the patient lying on it can be pushed by the drive of the coupling station 46 onto the support frame 44 and into the computer tomography system 40 and moved to the correct position required for the taking of the graphic picture.

The above-described process is run in the reverse sequence for the transfer of the support plate 20 to the operating table 10. As will be understood, there exists the possibility of taking control pictures by the computer tomography system even during the progress of an operation without having to unbed the patient from the operating table support surface to an undersurface with which he can then be moved into the computer tomography system, as has previously been the case.

Since the patient support means 12 should be releasably connected with the sub-frame, there exists also the possibility that the operating table 10 and the computer tomography system 40 can be associated with the support frame 44 in separate places. Should a control picture be wanted during an operation, the operation table support surface can in a known way be placed onto a carriage and moved to the computer tomography system, where then the transfer of the support plate to the support frame 44 takes place in the above described way.

The support frame 44 can be adjustable in height and as the case may be also adjustable to produce a specific positioning of the patient, for example, pivotal about a longitudinal or transverse axis. The operating table system of the invention is also useful in combination with other diagnostic devices such as NMR devices.

What is claimed is:

1. An operating table system for computer tomography assisted operations on patients, including an operating table (10) with a subframe (14) and a patient support surface means (12) releasably connected with the subframe (14), characterized in that, the patient support surface means (12) has a frame (16) connected with the subframe (14) and has an x-ray permeable patient support plate (20) longitudinally slidably guided in the frame (16), that a support frame (44) intended for the reception of the support plate (20) in a computer tomography system (40) is connected with a coupling station (46) coupable with the support plate (20) for the transfer of the support plate (20) from the subframe (14) of the operating table (10) to the support frame (44) and vice versa, that the subframe (14) is shiftable on a guide track (38) extending to the coupling station (46), that the subframe has at least two support columns carrying the frame (16), which support columns are movable relative to one another on the guide track (38), and that the frame (16) has two longitudinal beams (18) on which there are first guide tracks (22) for the support plate (20) and second guide tracks (28) for two cross beams (24) each connected with a respective one of the support columns.

2. An operating table system according to claim 1, further characterized in that the coupling station (46) has a drive (48) for shifting the support plate (20) from the subframe (14) to the support frame (44) and vice versa.

3. An operating table system according to claim 2, further characterized in that the drive is formed to shape-wise grip the support plate (20).

4. An operating table system according to claim 3, further characterized in that the drive includes at least a gear or a toothed belt driven by a motor designed for gripping engagement with a rack provided on the patient support plate (20).

5. An operating table system according to claim 2, further characterized in that the drive is for a forcewise gripping and transport of the support plate (20).

6. An operating table system according to claim 1, further characterized in that the patient support surface (12) is divided into several sections (30, 32, 34) which are connected with one another for pivotal movement about horizontal axes.

7. An operating table system according to claim 6, further characterized in that the sections of the support plate (20) pivotal relative to one another are connected with one another by x-ray permeable joints.

8. An operating table system according to claim 1, further characterized in that the subframe (14) is adjustable in height.

* * * * *